US008039612B2

United States Patent
Lorenz et al.

(10) Patent No.: US 8,039,612 B2
(45) Date of Patent: Oct. 18, 2011

(54) SYNTHESIS OF OLIGONUCLEOTIDES OR PHOSPHOROTHIOATE OLIGONUCLEOTIDE WITH A CAPPING AGENT OF N-METHYLIMIDAZOLE FREE OF 1,3,5-TRIMETHYLHEXAHYDRO-1,3,5-TRIAZINE

(75) Inventors: Sandra Lorenz, Grand Haven, MI (US); Jim Przybytek, West Olive, MI (US); Karel Snoble, Norton Shores, MI (US)

(73) Assignee: Honeywell International, Inc., Morristown, NJ (US)

( * ) Notice: Subject to any disclaimer, the term of this patent is extended or adjusted under 35 U.S.C. 154(b) by 365 days.

(21) Appl. No.: 12/249,538

(22) Filed: Oct. 10, 2008

(65) Prior Publication Data

US 2009/0099352 A1   Apr. 16, 2009

Related U.S. Application Data

(60) Provisional application No. 60/980,063, filed on Oct. 15, 2007.

(51) Int. Cl.
*C07H 21/00* (2006.01)
(52) U.S. Cl. .................................................. 536/25.34
(58) Field of Classification Search .................. None
See application file for complete search history.

(56) References Cited

U.S. PATENT DOCUMENTS

| | | | |
|---|---|---|---|
| 5,998,604 A | 12/1999 | Fearon et al. | |
| 6,426,184 B1 * | 7/2002 | Gao et al. | 435/6 |
| 6,762,298 B2 * | 7/2004 | Beaucage et al. | 536/25.31 |
| 6,965,041 B1 | 11/2005 | Beaucage et al. | |
| 7,169,916 B2 | 1/2007 | Krotz et al. | 536/25.3 |
| 7,476,709 B2 * | 1/2009 | Moody et al. | 525/118 |
| 2001/0044529 A1 | 11/2001 | Beaucage et al. | |
| 2004/0035690 A1 | 2/2004 | Gulari | |
| 2006/0036028 A1 | 2/2006 | Moody et al. | |

OTHER PUBLICATIONS

Sobczyk et al.; "Infrared and NMR Spectroscopic Studies of Hexhydro-1,3,5-Trialkyltriazines"; Chemia Stosowana (1973) 17 (3); pp. 359-366.

* cited by examiner

*Primary Examiner* — Lawrence E Crane

(57) ABSTRACT

According to the present invention, there is provided a process for making an oligonucleotide or a phosphorothioate oligonucleotide. The process has the following steps: (a) providing an amount of a blocked nucleotide; (b) deblocking the blocked nucleotide to form an unblocked nucleotide; (c) activating the deblocked nucleotide; (d) coupling the deblocked nucleotide with a phosphoramidite to form a phosphite oligomer; (e) capping any uncoupled deblocked nucleotide via reaction with an amount of acetic anhydride and an amount of N-methylimidazole that is substantially free of 1,3,5-trimethylhexahydro-1,3,5-triazine; (f) oxidizing the phosphite oligomer to form the oligonucleotide or sulfurizing the phosphite oligomer to form a phosphorothioate oligonucleotide; and (g) optionally repeating steps (b) through (f). There is also a process for capping a nucleotide.

3 Claims, 9 Drawing Sheets

US 8,039,612 B2

SYNTHESIS OF OLIGONUCLEOTIDES OR PHOSPHOROTHIOATE OLIGONUCLEOTIDE WITH A CAPPING AGENT OF N-METHYLIMIDAZOLE FREE OF 1,3,5-TRIMETHYLHEXAHYDRO-1,3,5-TRIAZINE

CROSS-REFERENCES TO RELATED APPLICATIONS

The present application claims the benefit of U.S. Provisional Application Ser. No. 60/980,063, filed on Oct. 15, 2007, currently expired, the disclosure of which is incorporated herein by reference in its entirety.

BACKGROUND OF THE INVENTION

1. Field of the invention

The present invention relates to a process for synthesizing oligonucleotides or phosphorothioate oligonucleotides while using a capping agent of N-methylimidazole substantially free of 1,3,5-trimethylhexahydro-1,3,5-triazine.

2. Description of the Related Art

Oligonucleotides and phosphorothioate oligonucleotides are synthesized via coupling of nucleotides. The synthesis generally has the following steps: (a) deblocking, (b) activation/coupling, (c) capping, and (d) oxidation (in the case of oligonucleotides) or sulfurization (in the case of phosphorothioate oligonucleotides). The cycle may be repeated sequentially depending on the number of bases to be coupled.

The capping step is commonly carried out in the presence of a combination of N-methylimidazole and acetic anhydride. In some oligonucleotide syntheses employing N-methylimidazole, it has been observed that some oligonucleotides having unwanted adducts may form. The adducts have been observed to add 85 daltons to the molecular weight of the oligonucleotides.

It would be desirable to have a method for synthesizing oligonucleotides or phosphorothioate oligonucleotides in which the end product is substantially free of unwanted adducts.

SUMMARY OF THE INVENTION

According to the present invention, there is provided a process for making an oligonucleotide or a phosphorothioate oligonucleotide. The process has the following steps: (a) providing an amount of a blocked nucleotide; (b) deblocking the blocked nucleotide to form a deblocked nucleotide; (c) activating the deblocked nucleotide; (d) coupling the deblocked nucleotide with a phosphoramidite to form a phosphite oligomer; (e) capping any uncoupled deblocked nucleotide via reaction with an amount of acetic anhydride and an amount of N-methylimidazole that is substantially free of 1,3,5- trimethylhexahydro-1,3,5-triazine; (f) oxidizing the phosphite oligomer to form the oligonucleotide or sulfurizing the phosphite oligomer to form a phosphorothioate oligonucleotide; and (g) optionally repeating steps (b) through (f).

Further according to the present invention, there is provided a process for capping a nucleotide having a hydroxyl site. The process has the step of reacting the nucleotide with an amount of acetic anhydride and an amount of N-methylimidazole that is substantially free of 1,3,5-trimethylhexahydro-1,3,5-triazine.

DETAILED DESCRIPTION OF THE INVENTION

Figure 1:
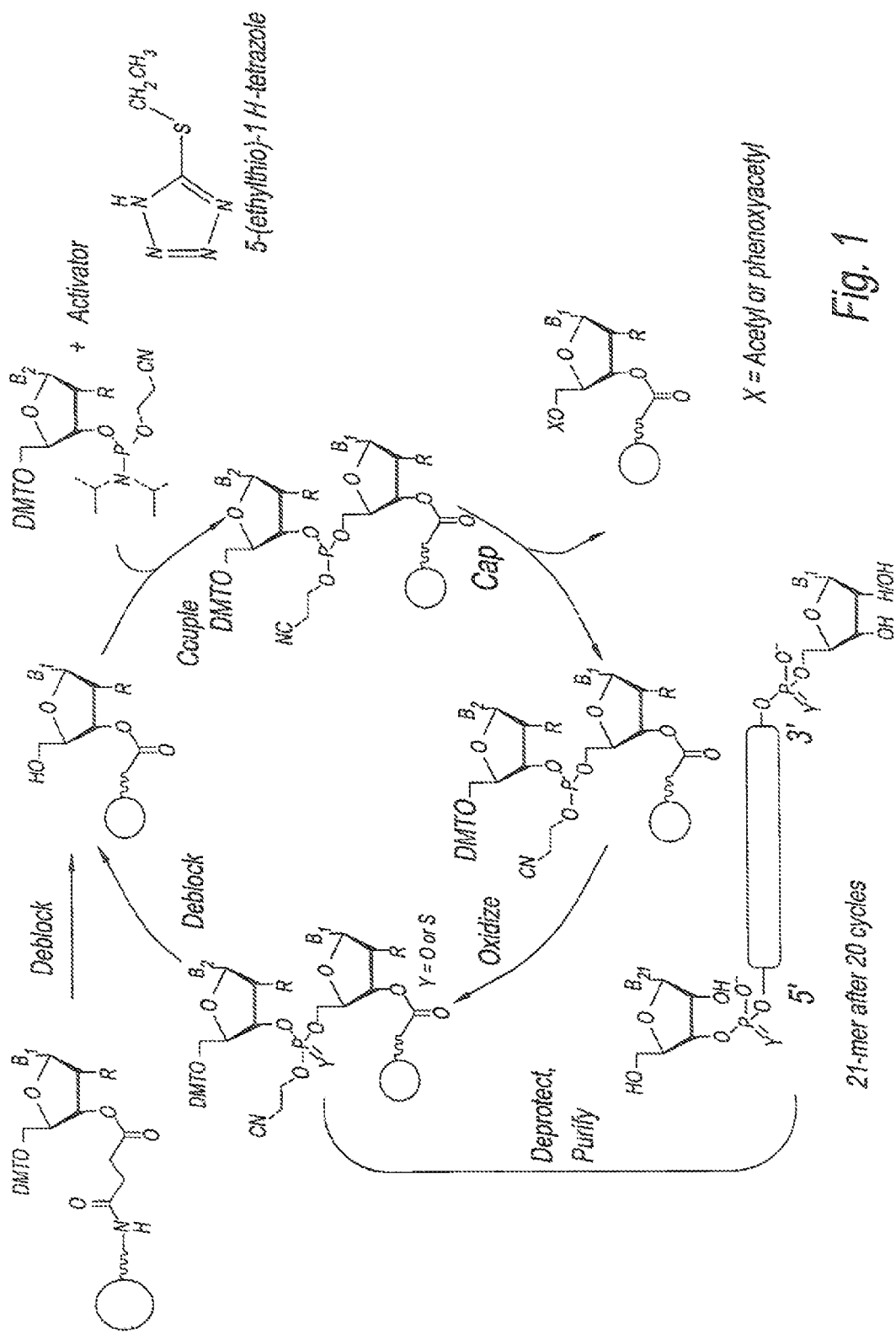
FIG. 1 is a cylic representation of an embodiment of the process of the present invention.

A source of unwanted adducts in product oligonucleotides has been identified as an impurity in N-methylimidazole, one of the capping agents used in the synthesis processes. The impurity has been found in some industrial lots of N-methylimidazole as 1,3,5-trimethylhexahydro-1,3,5-triazine and/or its Schiff base, N-methylenemethanamine. The two impurities are usually present in equilibrium in N-methylimidazole. For purposes of convenience and easy reference, the two impurities are referred to singularly as 1,3,5-trimethylhexahydro-1,3,5-triazine. The triazine content in N-methylimidazole has been observed to be as high as about 40 to about 70 ppm (parts per million parts by weight). The triazine may be identified in N-methylimidazole with analytical techniques such as gas chromatograph mass spectroscopy (GCMS) and proton NMR.

In the process of the present invention, the problem of impure N-methylimidazole was resolved by seeking industrial lots of N-methylimidazole that were substantially free of the triazine. Preferably, the N-methylimidazole has about 10 ppm or less of the triazine by weight based on the weight of the N-methylimidazole. Most preferably, the N-methylimidazole has about 1 ppm or less of the triazine.

In a first step of the process, a blocked nucleotide is provided. The blocked nucleotide initially used is preferably provided in a form covalently linked to a support, such as silica or a polymer. The blocked nucleotide is variously derived and selected from among available heterocyclic nucleic acid bases. The blocked nucleotide is deblocked to form a deblocked nucleotide. In one embodiment of the invention, the deblocking is preferably carried out via reaction with an amount of dichloroacetic acid in the presence of toluene or dichloromethane.

The deblocked nucleotide is then activated to prepare it for coupling with a phosphoramidite. Activation is carried out via contact with an activator.

After activation, the deblocked nucleotide is coupled, i.e., reacted, with a phosphoramidite to form a phosphite oligomer. The phosphoramidite is variously selected from among all available phosphoramidites. In formation of useful oligonucleotides, the coupling step will preferably be repeated until the desired oligonucleotide length is achieved.

Typically, during the coupling step, only a portion of the deblocked nucleotide react with the phosphoramidite. The unreacted nucleotides must be capped. Capping is carried out by reacting the unreacted nucleotides with an amount of acetic anhydride and an amount of N-methylimidazole that is substantially free of 1,3,5-trimethylhexahydro-1,3,5-triazine. The capped oligonucleotides are no longer available for subsequent nucleotide additions.

After capping, the phosphite oligomer is oxidized or sulfurized. In one embodiment of the process, the phosphite oligomer is oxidized via reaction with iodine in the presence of water and pyridine.

Additional disclosure concerning processes for making oligonucleotides is shown in U.S. Pat. No. 7,169,916 B2, which is incorporated herein by reference.

The features of the present invention will be made more apparent by the following examples, which are not to be construed as limiting.

EXAMPLES

Example 1

Phosphorothioate oligonucleotides can be synthesized while using a capping agent of N-methylimidazole substantially free of 1,3,5-trimethylhexahydro-1,3,5-triazine according to the process of the present invention.

Figure 2:
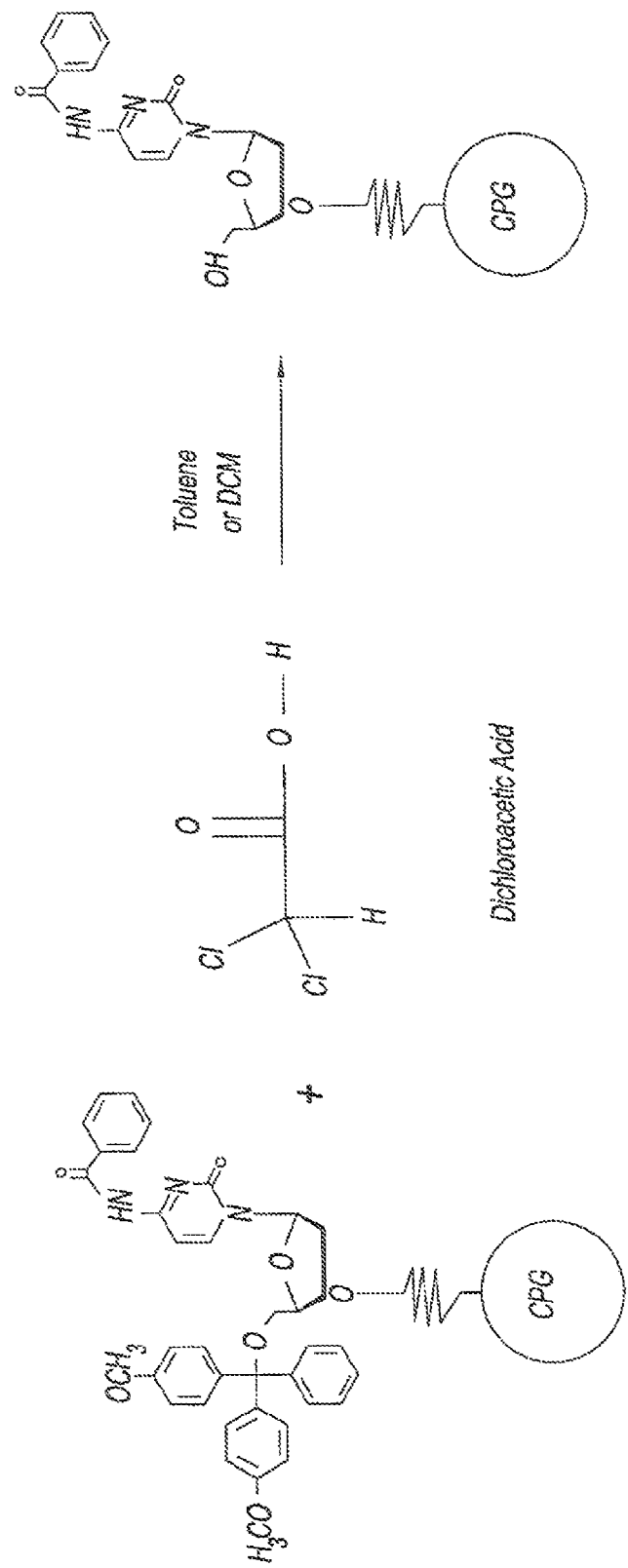
FIG. 2 is a representation of a deblocking step of the process of the present invention.

Referring to FIG. 2, the first base, a cytidine nucleotide, which is attached to a CPG solid support, is at first inactive because all the active sites have been protected. To add the next base, the dimethoxytrityl (DMT) group protecting the 5'-hydroxyl group must be removed (the deblocking step). Addition of 3% DCA in DCM (or in toluene) removes the DMT group and allows the 5'-hydroxyl group to become the reactive site.

Figure 3:
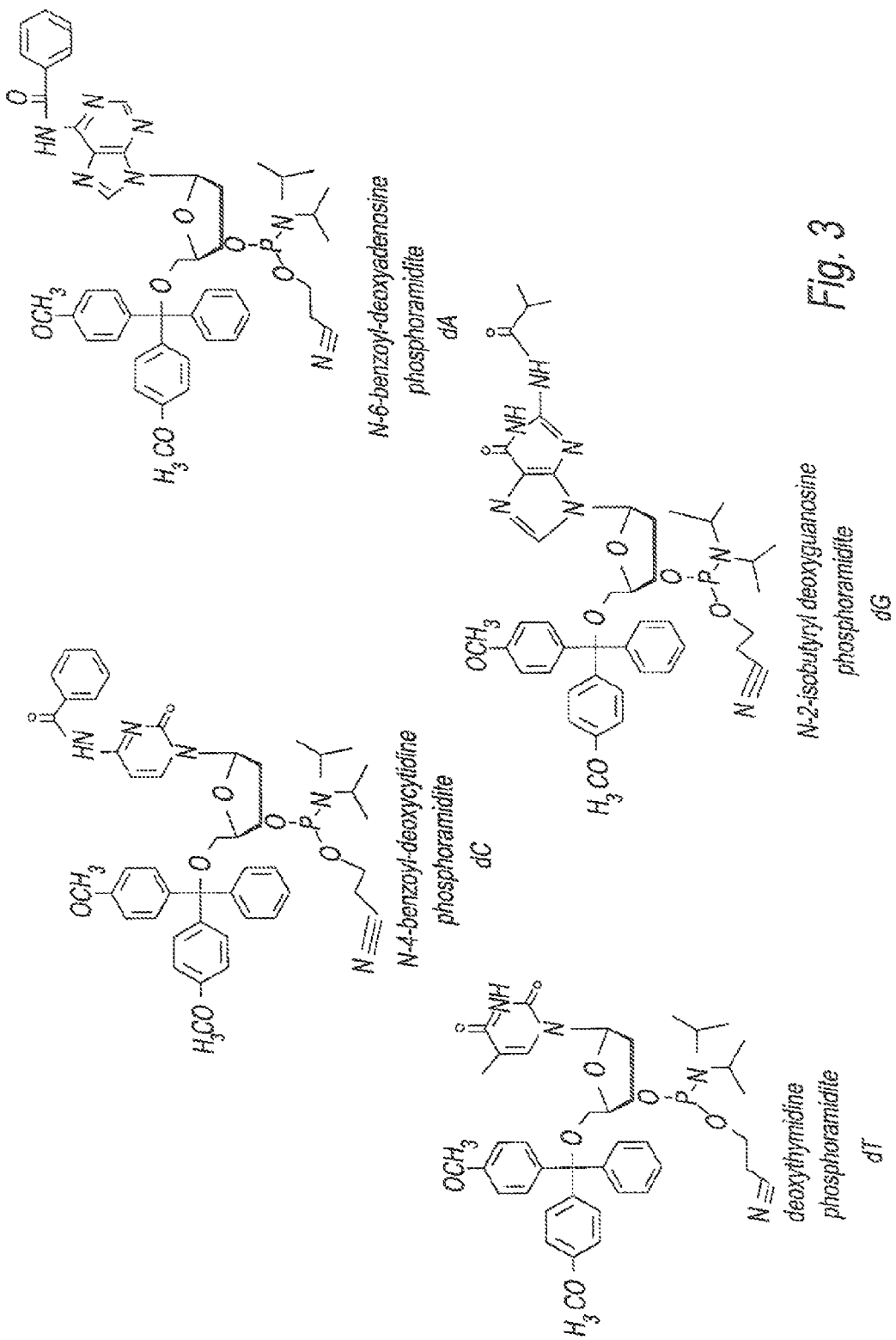
FIG. 3 is a representation of an activation and coupling step of the process of the present invention. The acronym "CPG" stands for controlled pore glass.

The next base monomer cannot be added until it has been activated (the activation step). This is achieved by adding an activator, such as a tetrazole-based activator like 5-ethylthiotetrazole, to the column. The active 5'-hydroxyl group of the preceding base and the newly activated phosphorus bind to loosely join the two bases together. This forms an unstable phosphite linkage. The reaction column is then washed with acetonitrile to remove any extra activator, unbound phosphoramidite and by-products. There are four DMT-protected nucleotides (phosphoramidites) are depicted in FIG. 3.

Figure 4:
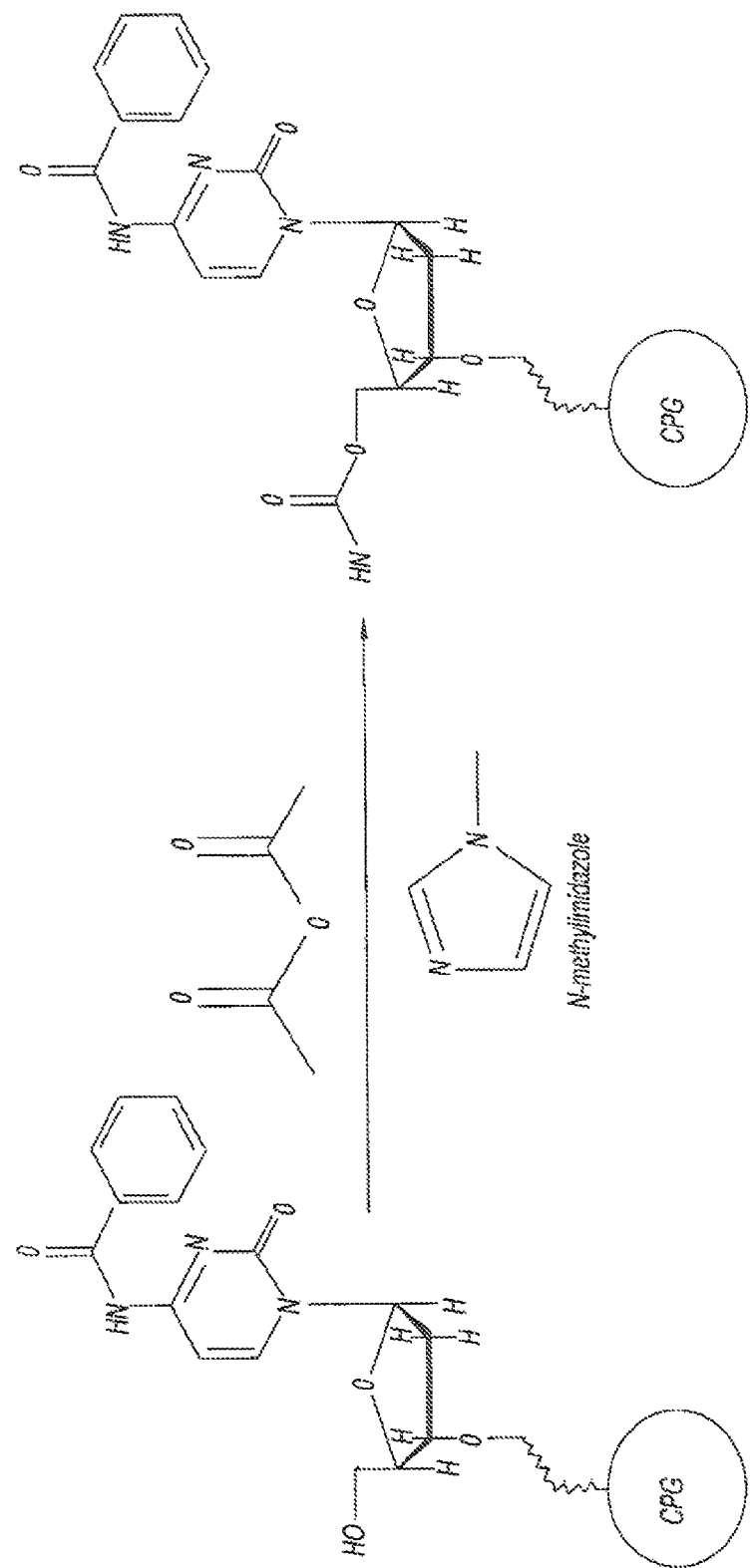
FIG. 4 is a representation of a capping step of the process of the present invention.

Any of the first bases that failed to react are capped with NMI as depicted in FIG. 4 (the capping step). These failed bases will play no further part in the synthesis cycle. The base on the left (already attached to the solid support) did not bind to a base in the activation step. The unreacted 5'-hydroxyl is blocked from further reactions by acetylation.

In the activation step, the next desired base was added to the previous base, which results in an unstable phosphite linkage. To stabilize this linkage, an oxidizing solution of dilute iodine in water and pyridine is added to the reaction column. The unstable phosphite linkage is oxidized to form a more stable phosphate linkage (the oxidation step).

Figure 5:
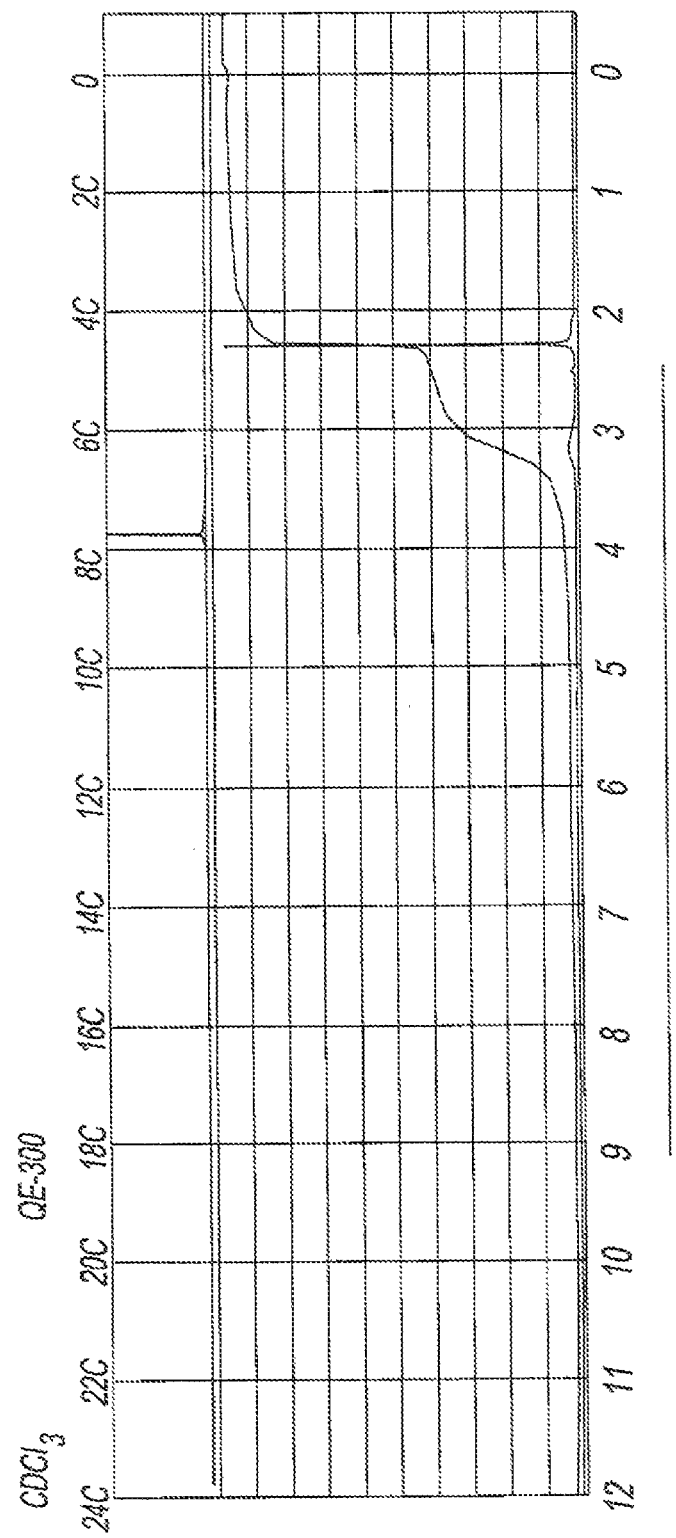
FIG. 5 is a representation of an $^1$H NMR spectra of 1,3,5-trimethylhexahydro-1,3,5-triazine.
Figure 8:
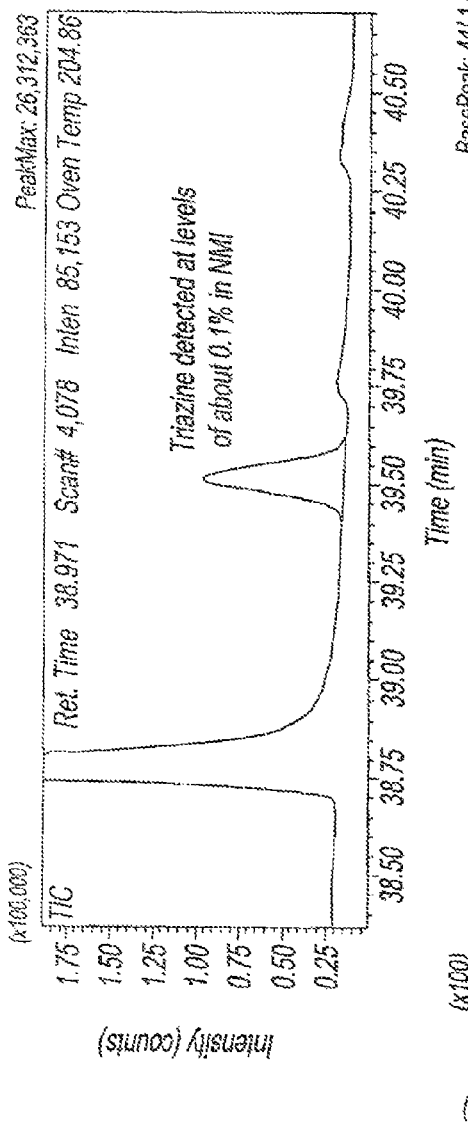
FIGS. 8 to 10 are representations of GCMS peaks of 1,3,5-trimethylhexahydro-1,3,5-triazine.
Figure 9:
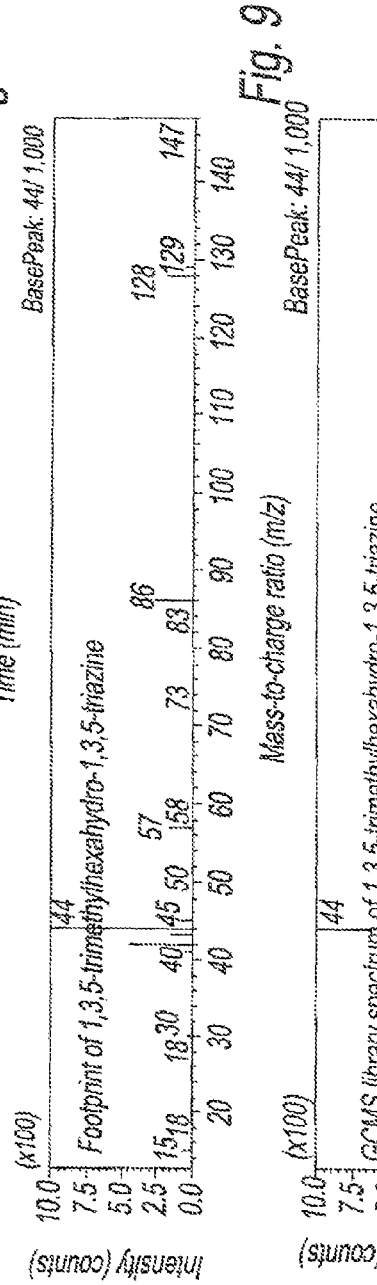
Figure 10:
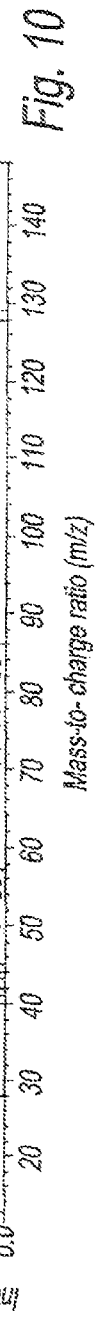

An $^1$H NMR spectrum for 1,3,5-trimethylhexahydro-1,3,5-triazine as taken from the website of Sigma Aldrich (SIAL.COM) is depicted in FIG. 5. GCMS profiles for 1,3,5-trimethylhexahydro-1,3,5-triazine are shown in FIGS. 8 to 10. Identified GCMS peaks for 1,3,5-trimethylhexahydro-1,3,5-triazine are set forth in Table 1 below.

TABLE 1

| Retention Time (min) | Peak ID |
|---|---|
| 8.3 | water |
| 9.5 | ethyleneimine (N-methylenemethanamine) |
| 25.4 | ethylene glycol |
| 27.0 | N-methyl formamide |
| 27.3 | 2-methyl-1-butanol |
| 27.4 | N-methyl formamide |
| 28.7 | 1-pentanol |
| 36.1 | NMI |
| 38.8 | 1,4-dimethylimidazole |
| 39.5 | 1,3,5-trimethylhexahydro-1,3,5-triazine |
| 41.2 | 2-octanol |
| 42.4 | 1,2-dimethylimidazole |
| 43.0 | 1-methyl-2-piperidinone |
| 43.7 | 2-methyl-2,4-pentanediamine |
| 45.0 | 1,3-dimethyl-2-(1-methylethyl)cyclopentene |
| 48.1 | hexahydro-1-methyl-1-H-azepin-2-one |

Figure 6:
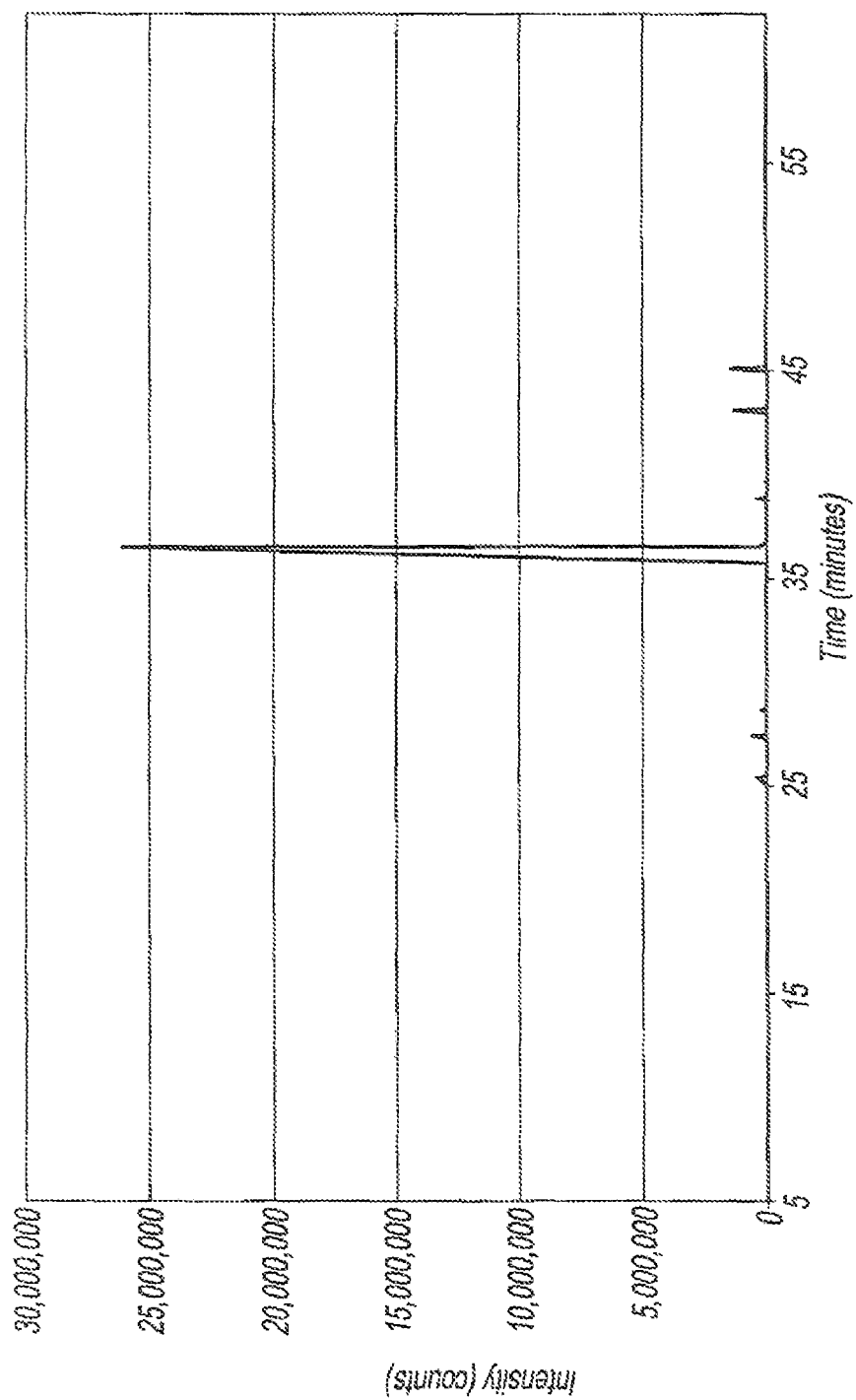
FIGS. 6 and 7 are representations of an impurity profile of an industrial lot of N-methylimidazole obtained via GCMS chromatogram.
Figure 7:
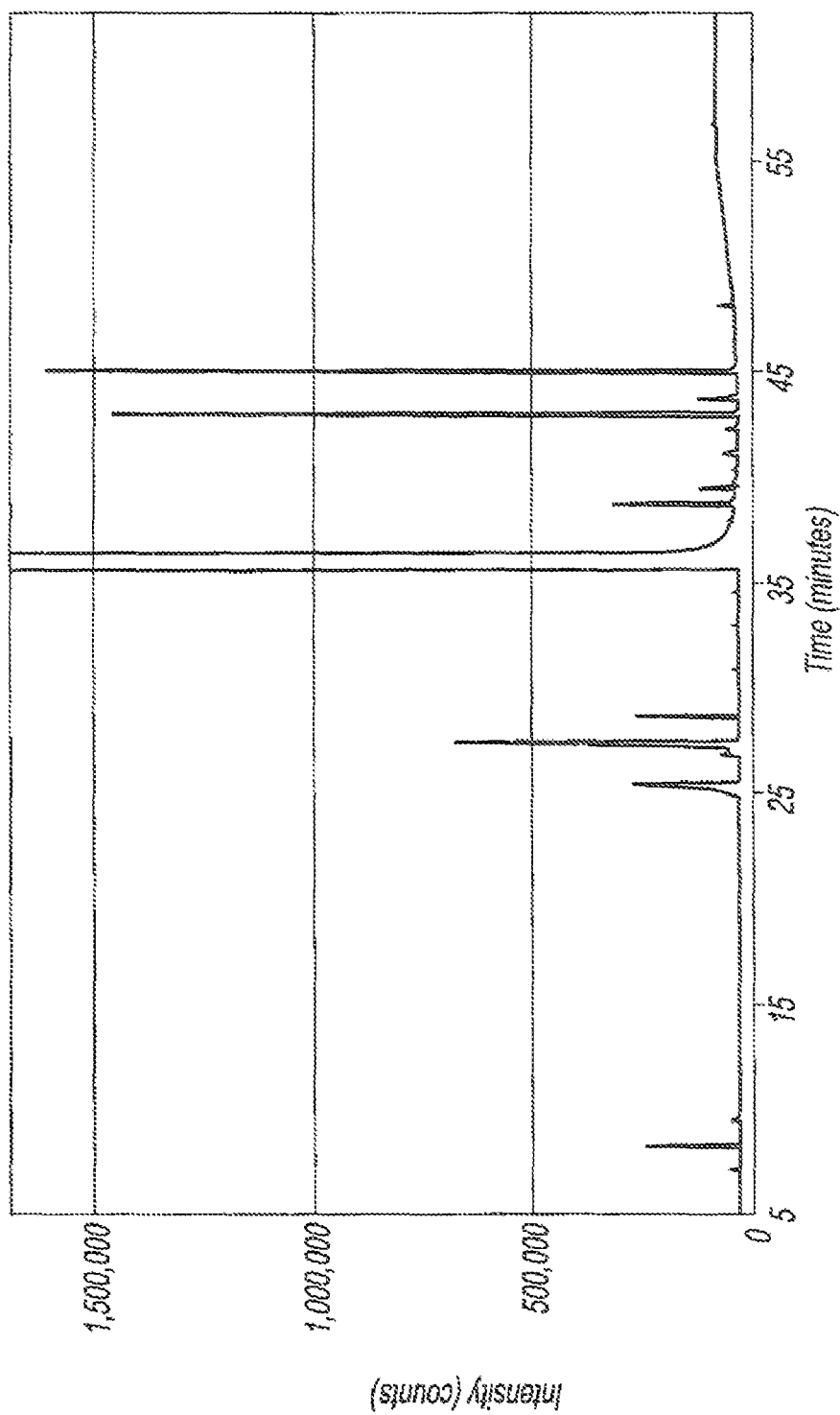

A GCMS Chromatogram showing Total Ion Counts in the NMI is depicted in FIG. 6. A GCMS Chromatogram showing total ion counts on an expanded scale so impurity peaks are visible is depicted in FIG. 7. Data was collected with a Shimadzu GCMS 2010.

Figure 11:
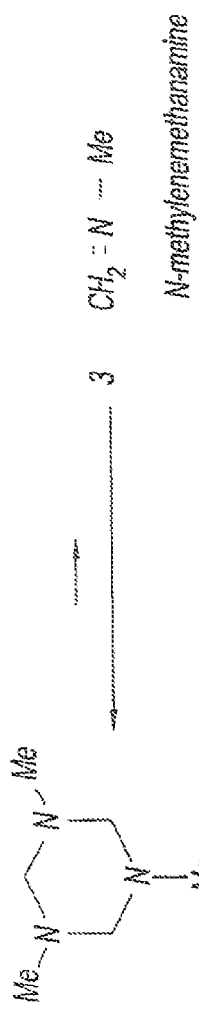
FIG. 11 is a representation of 1,3,5-trimethylhexahydro-1,3,5-triazine in equilibrium with its Schiff base.

A equilibrium expression of 1,3,5-trimethylhexahydro-1,3,5-triazine and its Schiff base is shown in FIG. 11. The expression was taken from Infrared and NMR Spectroscopic Studies of Hexhydro-1,3,5-Trialkyltriazines, *Chemia Stosowana* (1973), 17(3), 359-66.

Figure 12:
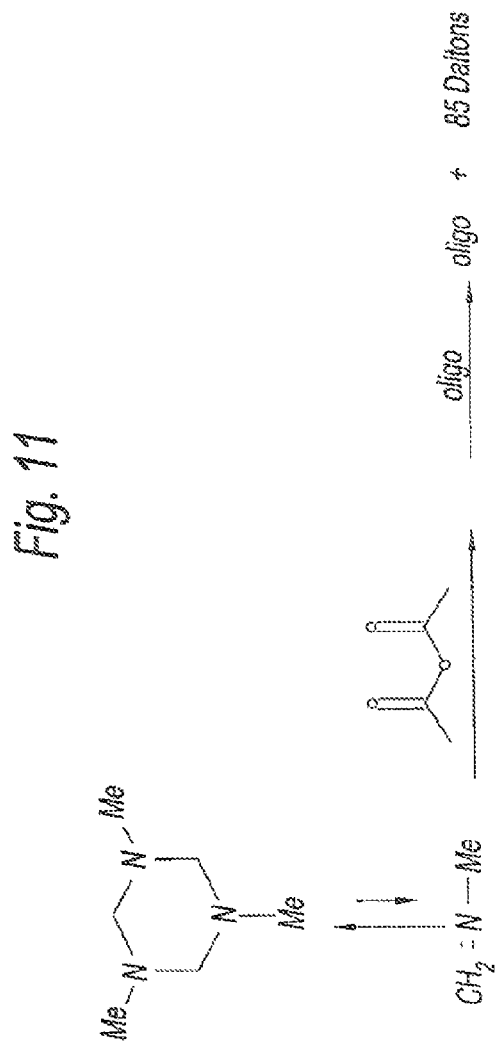
FIG. 12 is a representation of the process of forming an oligonucleotide adduct.

FIG. 12 shows a representation of an oligomerized product of 1,3,5-trimethylhexahydro-1,3,5-triazine.

Example 2

DNA is synthesized according to the procedure and with ingredients set forth in Tables 2 and 3.

TABLE 2

| Detritylation | Deblock solution |
|---|---|
| Coupling | Activator solution |
| Capping | Capping A & B |
| Oxidation | Oxidation Solution |
| Cleavage | Ammonia (RT) |
| Deprotection | Ammonia (@ 65° C. |
| Purification | HPLC (Buffers) |

TABLE 3

| Reagent | Formulation |
|---|---|
| Detritylation Solution | 3.0% Dichloroacetic Acid in Dichloromethane (v/v) |
| Detritylation Solution | 3.0% Dichloroacetic Acid in Toluene (v/v) |
| ETT Activator | 0.25M 5-Ethylthio-1H-tetrazole (ETT) in Acetonitrile |
| BMI Activator | 0.3M BMT with 0.5% NMI in acetonitrile |
| Oxidation Solution | 0.05M Iodine in 90% Pyridine and 10% Water (v/v) |
| Capping A Solution | 20% N-Methylimidazole and 80% Acetonitrile (v/v) |
| Capping B Solution | 20% Acetic Anhydride, 30% 2,6-Lutidine and 50% Acetonitrile (v/v/v) |
| Scavenger for Acrylnitrile | 20% Diethylamine in acetonitrile (v/v) |

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. An improved process of making oligonucleotides that includes steps of deblocking blocked nucleotide having a dimethoxytrityl group blocking a 5'-hydroxyl group, activating the deblocked nucleotide, reacting deblocked nucleotide with a phosphoramidite to form phosphite oligomer, and capping unreacted deblocked nucleotide, wherein the improvement comprises capping unreacted deblocked nucleotide by reacting the unreacted deblocked nucleotide with an amount of acetic anhydride and an amount of N-methylimidazole that is substantially free of 1,3,5-trimethylhexahydro-1,3,5-triazine.

2. The process of claim 1, wherein the wherein the N-methylimidazole has a content of about 10 ppm or less 1,3,5-trimethylhexahydro-1,3,5-triazine based on the weight of the N-methylimidazole.

3. The process of claim 1, further comprising wherein the process steps are repeated until the desired oligonucleotide length is achieved.

* * * * *